United States Patent [19]

Shimamoto et al.

[11] Patent Number: Plant 6,449

[45] Date of Patent: Dec. 6, 1988

[54] PITTOSPORUM PLANT 'SHIMAMOTO'

[76] Inventors: George Shimamoto; Alan Shimamoto, both of 932 Beach St., Montebello, Calif. 90640

[21] Appl. No.: 929,010

[22] Filed: Nov. 17, 1986

[51] Int. Cl.[4] ..... A01H 5/00
[52] U.S. Cl. ..... Plt./54
[58] Field of Search ..... Plt./54

[56] References Cited

U.S. PATENT DOCUMENTS

P.P. 4,919 11/1982 Turner ..... Plt. 54
P.P. 5,233 5/1984 Turner ..... Plt. 54
P.P. 5,893 3/1987 Rackley ..... Plt. 54

*Primary Examiner*—James R. Feyrer

[57] ABSTRACT

A Pittosporum plant possessing a dwarf habit of growth, and medium green elongated leaves with irregular variegated margins separating creamy white tips.

2 Drawing Sheets

DESCRIPTION OF THE INVENTION

The present invention is a distinct, new and improved variety of the Pittosporum Tobira Wheeler's Dwarf plant ("Wheeler's Dwarf"), which was originated and discovered by us as a cultivated sport in order to promote the progress of science and the useful arts.

In or about the Winter of 1979, at our nursery in Montebello, Calif., George Shimamoto discovered the sport growing on one of our Wheeler's Dwarf plants. It was apparent that the sport had distinct characteristics from the parent plant because the leaves of the sport, unlike the dark green leaves of the parent plant, were variegated and medium green in color with Cream white margins.

George Shimamoto performed an initial experiment to determine the sport's capacity to asexually reproduce. George Shimamoto made three (3) cuttings from the sport, all of which rooted and survived. Each cutting possessed the same characteristics as the sport, and constituted a distinct, new and improved variety of Pittosporum.

After the success of the initial experiment, George Shimamoto further experimented by duplicating the above stated procedure. The second experiment involved cuttings from both the sport and the original three cuttings. All of the cuttings rooted and survived, and each cutting possessed the same characteristics as the sport.

Since the initial experiment, we have continued to propagate our plants, and now currently possess in excess of 100,000 separate and distinct variegated Pittosporum plants.

It is our opinion, and the opinion of agricultural and horticultural experts, that our plant ("Shimamoto Pittosporum") is a distinct, new and improved variety of Pittosporum and is sufficiently useful and important. The principal characteristics which distinguish the Shimamoto Pittosporum and make it sufficiently useful and important are:

(1) Its ability to asexually reproduce and maintain its unique characteristics through succeeding propagations;

(2) Its dwarf size makes it appropriate for use: as a border plant, a small hedge, in planter boxes and as a pot plant;

(3) Its slow rate of growth results in minimal maintenance by eliminating frequent pruning;

(4) Its slow rate of growth results in a longer retention of an aesthetically pleasing shape;

(5) A shrub possessing several colors due to its variegated nature of elongated evergreen leaves;

(6) Elongated evergreen leaves consisting of a medium green color with irregular variegated margins separating its creamy white tips; and (7) Its leaves grow in a whorl on the branches, due to an alternate pattern of growth.

The submitted drawings and photographs are correct and accurate depictions of the Shimamoto Pittosporum, containing both young and mature leaves.

The following is a detailed description of our new variety of pittosporum, with color numbers in accordance with the Pantone Matching System of colors for printing inks, 17th edition, published by Pantone, Inc., 1982. Terms used to describe colors are those of ordinary significance.

THE PLANT (1) Parentage: A cultivated sport cutting from a *Pittosporum tobira* Wheeler's Dwarf.

(2) Size: A dwarf with its height and width between 0.50 to 0.75 meters.

(3) Growth habit: The Shimamoto Pittosporum has a slow rate of growth. It grows full from just above ground level upward, with the width of the plant about the same as the height.

(4) Hardiness: The Shimamoto Pittosporum is most suitable in Zones 9 and 10 of the U.S. Department of Agriculture Hardiness Map. This Hardiness Map depicts the temperature zones within the United States. Zones 9 and 10 cover the Southern part of the United States, from California to Florida, encompassing temperatures ranging from 20 to 30 degrees Fahrenheit.

The Shimamoto Pittosporum possesses the ability to tolerate droughts. However, it is not known whether it could withstand prolonged and/or freezing weather, or violet salient winds.

(5) Branches: The Shimamoto Pittosporum is densely branched from just above ground level, and there is branching at each node. While the main branches ascend, the plant does not develop a central leader or trunk.

The new growth of branches begin as light green. As the branch descends, the color changes to dark green, and later to dark brown as they mature.

(6) Foliage:

(a) *Type.*—Elongated evergreen; petioled; and grow alternately in a whorl on the branches.

(b) *Shape.*—Oblanceolate with entire margins; apex and base are acuminate.

(c) *Petioles.*—Length — from about 3 to 5 mm; color light green.

(d) *Leaf size.*—Length of mature leaf from about 40 to 80 mm; width of mature leaf about 13 to 25 mm. The size of the leaf varies according to sunshine conditions at the time the leaf is produced, with larger leaves being produced under cloudy conditions, as opposed to sunny conditions.

(e) *Venation.*—Pinnately; under surface midrib is prominent and readily apparent; upper surface midrib is clearly visible and pronounced, and is of a lighter color than surrounding areas of the leaf; lateral veins are not readily apparent.

(f) *Leaf color.*—Mature leaves — Upper surface is medium green, Color No. 575U; with variegated margins of cream white, Color No. 586U; the irregular line of intersection between the green of the central area and the cream white margin is relatively sharp, the width of the margin varying from about 1 to 10 mm; Under surface (similar to the upper surface) is dark green, Color No. 577U with marginal variegations light green, Color 587U; nature and width of margins same as on mature leaves. Most of the variegation is on the outer half of the leaf blade.

(g) *Leaf texture.*—Tough, leathery; smooth; Upper surface is semi-glossy; Lower surface is dull.

(h) *Flowers.*—Neither the parent plant, nor the Shimamoto Pittosporum has yet to produce any flowers. However, based upon our agricultural experience, we are informed and believe that flowers may appear on an unpruned plant.

DISTINGUISHED FROM OTHER *PITTOSPORUM TOBIRA'S*

(1) *Pittosporum tobira* Wheeler's Dwarf:

(a) *Size.*—The Shimamoto Pittosporum is similar in size to the Wheeler's Dwarf.

(b) *Growth habit.*—The Shimamoto Pittosporum is slower growing than the Wheeler's Dwarf.

(c) *Color of leaves.*—The color of the leaves on the Shimamoto Pittosporum is of a lighter shade of green than the Wheeler's Dwarf.

(d) *Variegated leaf blades.*—The Wheeler's Dwarf does not possess the variegated nature of the leaf blades as the Shimamoto Pittosporum.

(2) *Pittosporum tobira* Variegata:

(a) *Size.*—The Shimamoto Pittosporum possesses a dwarf size, whereas the Variegata does not possess a dwarf nature.

(b) *Growth habit.*—The Shimamoto Pittosporum is slower growing than the Variegata.

(c) *Color of variegated margins on leaves.*—The Shimamoto Pittosporum and the Variegata are similar with respect to the color of the margins of their leaves.

(d) *Variegated leaf blades.*—The Shimamoto Pittosporum and the Variegata both have variegated leaf blades.

(3) Turner's Variegated Pittosporum: U.S. Plant Pat. No. 4,919 (Nov. 2, 1982).

(a) *Size.*—The Shimamoto Pittosporum is shorter than the predicted ultimate 1.5 to 2 meters of Turner's Pittosporum in attaining a size of only 0.50 to 0.75 meters.

(b) *Growth habit.*—The growth rate and ultimate plant shape of the Shimamoto Pittosporum is comparable to the Turner Pittosporum, but the ultimate size is smaller.

(c) *Color of margin on leaves.*—The color of the margin on the leaves of the Shimamoto Pittosporum is creamy white, whereas the color for the Turner's Pittosporum is pale yellow.

(d) *Variegated leaf blades.*—The Shimamoto Pittosporum is similar to the Turner Pittosporum with respect to its variegated leaf blades.

(e) *Shape of leaves.*—The shape of the leaves on the Shimamoto Pittosporum is elongated, whereas the shape of the leaves on the Turner Pittosporum is oblong.

(4) Turner's Tricolor Pittosporum: U.S. Plant Pat. No. 5,233 (May 15, 1984).

(a) *Size.*—The Shimamoto Pittosporum is shorter than the predicted ultimate 1.5 to 2 meters of the Tricolor in attaining only 0.50 to 0.75 meters.

(b) *Growth habit.*—The growth rate and ultimate plant shape of the Shimamoto Pittosporum is comparable to the Tricolor, but the ultimate size is smaller.

(c) *Color of margin on leaves.*—The color of the margin on the leaves of the Shimamoto Pittosporum is creamy white, whereas the color for the Tricolor is pale yellow. The Tricolor expresses patterns in two distinct green hues while the Shimamoto Pittosporum does not.

(d) *Variegation pattern.*—The Tricolor expresses patterns in three distinct colors while the Shimamoto Pittosporum has only two, one being creamy white, which is not expressed by the Tricolor.

(e) *Shape of leaves.*—The leaves of the Shimamoto Pittosporum are more elongated than those of the Tricolor.

(5) Rackley's "Lauralee" Pittosporum: U.S. Plant Pat. No. 5,893 (Mar. 3, 1987).

(a) *Size.*—The size of the Lauralee approaches the size of the *Pittosporum tobira* Wheelerii, whereas the Shimamoto Pittosporum attains a size between 50 and 75 cm.

(b) *Growth habit.*—The Lauralee is more sprawling and less upright than the Shimamoto Pittosporum, which attains a height and width which are generally nearly equal.

(c) *Variegation.*—The Shimamoto Pittosporum expresses a medium green and creamy white tip variegated coloration with no distinct spotting. However, the Lauralee is reliably distinguished because of its dark green spotting over medium green and light color pattern variegated leaves.

(d) *Leaf shape.*—The Shimamoto Pittosporum has leaves slightly longer and wider than those of the Lauralee, but are comparable in placement on the stem and in attitude when compared to the Lauralee; venation is comparable.

We claim:

1. A distinct, new and improved variety of *Pittosporum tobira* named Shimamoto Pittosporum, substantially as herein shown and described and which is principally distinguishable by:

(a) its ability to asexually reproduce and maintain its unique characteristics through succeeding propagations;

(b) a dwarf size which makes it appropriate for use as a border plant, a small hedge, in planter boxes and as a pot plant;

(c) a slow rate of growth resulting in minimal maintenance by eliminating frequent pruning and longer retention of an aesthetically pleasing shape;

(d) a shrub possessing several colors due to its variegated nature of elongated evergreen leaves;

(e) leaves consisting of a medium green color with irregular variegated margins separating its creamy white tips; and (f) leaves that grow in a whorl on the branches due to an alternate pattern of growth.

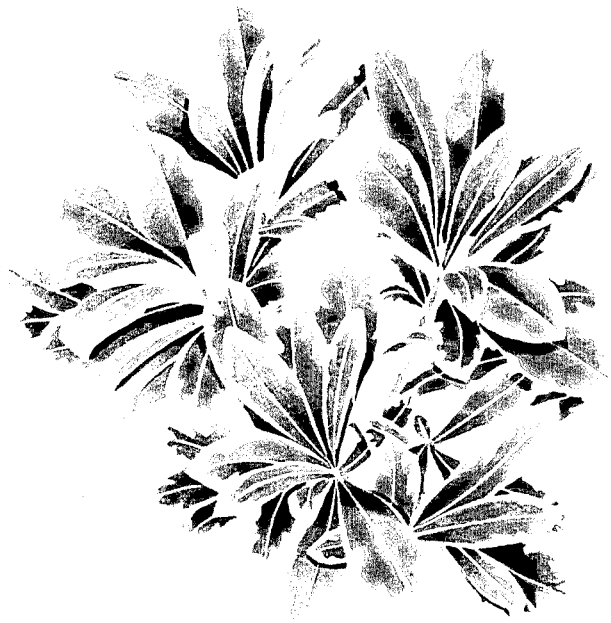
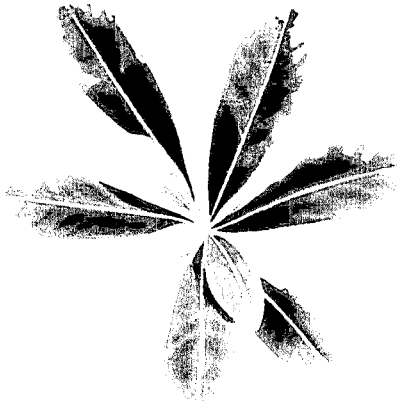

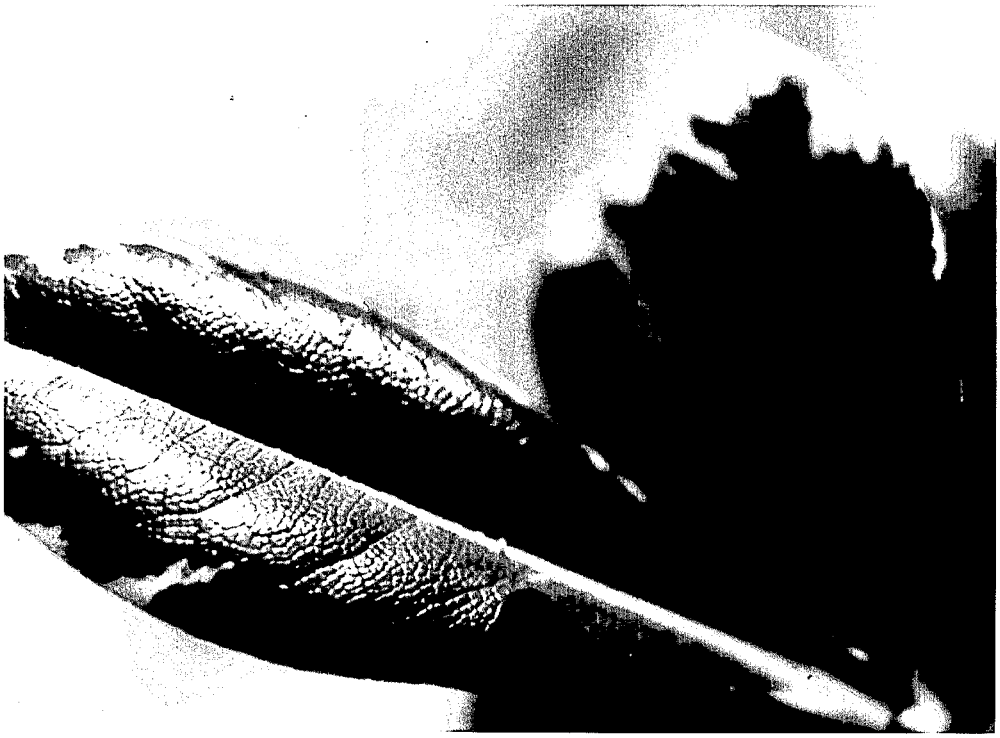
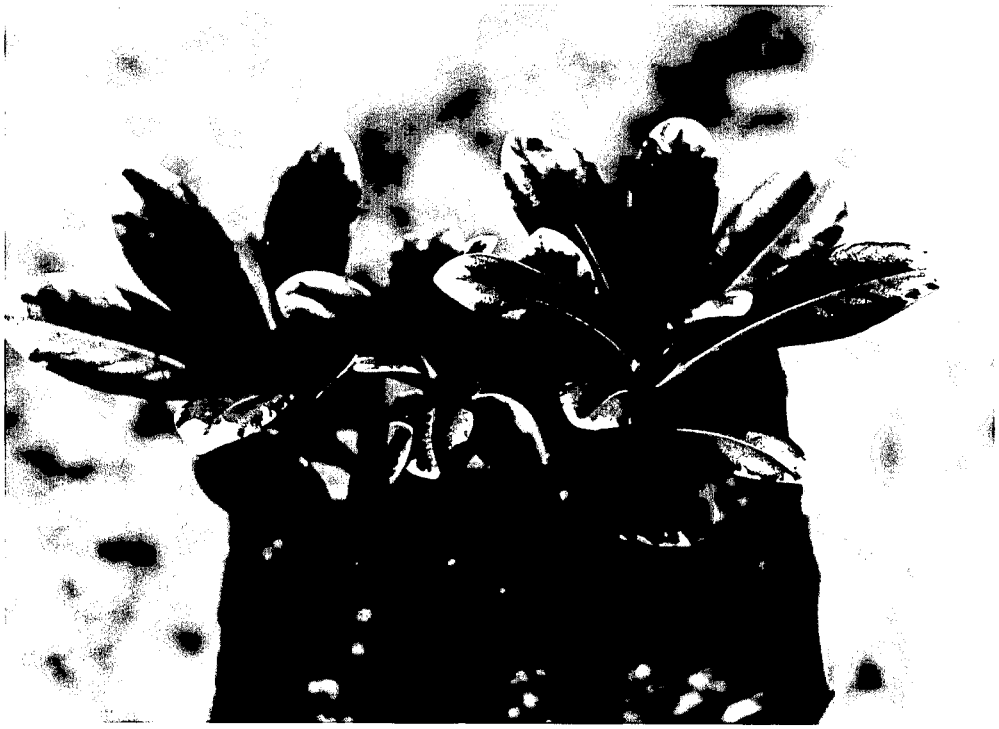

* * * * *